United States Patent
Johnstone et al.

(10) Patent No.: US 11,564,841 B2
(45) Date of Patent: Jan. 31, 2023

(54) HEARING PROTECTION HEADSET

(71) Applicant: JSP LIMITED, Witney (GB)

(72) Inventors: Clive Johnstone, Witney (GB); Stephen Sanders, Witney (GB)

(73) Assignee: JSP LIMITED, Witney (GB)

( * ) Notice: Subject to any disclaimer, the term of this patent is extended or adjusted under 35 U.S.C. 154(b) by 0 days.

(21) Appl. No.: 17/624,876

(22) PCT Filed: Jul. 2, 2020

(86) PCT No.: PCT/GB2020/051584
§ 371 (c)(1),
(2) Date: Jan. 5, 2022

(87) PCT Pub. No.: WO2021/005336
PCT Pub. Date: Jan. 14, 2021

(65) Prior Publication Data
US 2022/0273494 A1    Sep. 1, 2022

(30) Foreign Application Priority Data

Jul. 5, 2019 (GB) ...................................... 1909678

(51) Int. Cl.
*A61F 11/06* (2006.01)
*A61F 11/14* (2006.01)
(Continued)

(52) U.S. Cl.
CPC ............ *A61F 11/145* (2022.01); *G06F 3/165* (2013.01); *H04R 1/105* (2013.01); *H04R 1/1008* (2013.01);
(Continued)

(58) Field of Classification Search
CPC ..... A61F 11/145; G06F 3/165; H04R 1/1008; H04R 1/1025
See application file for complete search history.

(56) References Cited

U.S. PATENT DOCUMENTS

D725,031 S    3/2015  Tinius
D763,518 S    8/2016  Fletcher et al.
(Continued)

FOREIGN PATENT DOCUMENTS

AU        13708/2015         7/2015
EM     001245690-00002       7/2010
(Continued)

*Primary Examiner* — Simon King
(74) *Attorney, Agent, or Firm* — Dickinson Wright PLLC; Andrew D. Dorisio (57) ABSTRACT

A headset, comprising: first and second ear cups, and a power and signal connector that extends between the ear cups, wherein each ear cup comprises a housing having a mounting structure for mounting the ear cup on a wearable support; a speaker; and a speaker drive circuit for operating the speaker. The first ear cup further comprises: an external power and signal connector; and a mounting structure having a first profile for mounting a removable control module having a corresponding first profile on the first ear cup such that corresponding power and signal connectors can engage the external power and signal connector so that the removable control module can provide operating signals to the speaker drive circuits. The second ear cup comprises an external power connector; and a mounting structure having a second profile for mounting a removable battery pack having a corresponding second profile on the second ear cup such that a corresponding power connector on the battery pack can engage the external power connector so that the removable battery pack can provide power to the control module via the power and signal connector.

13 Claims, 6 Drawing Sheets

(51) Int. Cl.
*G06F 3/16* (2006.01)
*H04R 1/10* (2006.01)

(52) U.S. Cl.
CPC ......... *H04R 1/1025* (2013.01); *H04R 1/1033* (2013.01); *H04R 1/1041* (2013.01); *H04R 1/1083* (2013.01)

(56) References Cited

U.S. PATENT DOCUMENTS

| | | |
|---|---|---|
| 2005/0220318 A1 | 10/2005 | Han |
| 2009/0154740 A1 | 6/2009 | Regen et al. |
| 2009/0323975 A1* | 12/2009 | Groesch ............... H04R 1/1091 381/71.1 |
| 2014/0259287 A1* | 9/2014 | Waters ............... A41D 13/0002 2/209 |
| 2016/0080853 A1 | 3/2016 | Chen |
| 2016/0196100 A1 | 7/2016 | Yow et al. |
| 2017/0324437 A1* | 11/2017 | Ruttler ................... A61B 5/145 |
| 2018/0014972 A1* | 1/2018 | Fletcher ............... H04R 1/1008 |

FOREIGN PATENT DOCUMENTS

| | | | |
|---|---|---|---|
| JP | 2006121455 A | 5/2006 | |
| WO | 2005051255 A1 | 6/2005 | |
| WO | 2008122081 A1 | 10/2008 | |
| WO | 2009131518 A1 | 10/2009 | |
| WO | 2016126476 A1 | 8/2016 | |
| WO | WO-2017146671 A1 * | 8/2017 | |
| WO | WO-2020214085 A1 * | 10/2020 | .......... F21V 33/0056 |

\* cited by examiner

HEARING PROTECTION HEADSET

TECHNICAL FIELD

This invention relates to hearing protection headsets (sometimes call "ear defenders") that can be used by operators in noisy environments to protect against hearing damage. In particular, the invention relates to such headsets with built-in speakers for providing audio output to the wearer.

BACKGROUND ART

There have been previous proposals for active ear defender systems that involve electronic functionality to interact and/or manage the process of damping or changing noise heard by a user. WO 2016/126476 A (3M INNOVATIVE PROPERTIES COMPANY) Nov. 8, 2016 discloses a hearing protection device. The hearing protection device can include a speaker to relay sounds, such as conversations, to the user of the hearing protection. The hearing protection device can be powered by a rechargeable battery pack or separately by standard batteries. EP 1689337 A (PELTOR AB) 16 Aug. 2006 discloses a hearing protector comprising a hearing hood, a microphone, a loudspeaker and an amplifier. The hearing hood has passive noise damping. The microphone is disposed exteriorly on the hearing protector, while the loudspeaker is disposed inside the hood. The amplifier amplifies and transmits the signals from the microphone to the loudspeaker. The noise damping of the hearing hood is broad band. The frequency range of the amplifier corresponds to the frequency range of human speech. The amplification of the amplifier is variable and the greatest amplification is such that the sum total of the sound levels that are caused, on the one hand, by ambient sound passing through the hood and, on the other hand, by sound from the loudspeaker amounts to a maximum, predetermined value. Ear defender systems are also disclosed in WO 2009/131518 A (SPERIAN) and WO 2008/122081 A (SENSEAR).

A problem with previous active ear defender systems is that they are often configured for a specific use or environment and so may not be suitable when the use or environment changes.

This invention aims to provide a headset with improved configurability to address changing needs.

DISCLOSURE OF INVENTION

The invention provides a headset, comprising:
first and second ear cups, wherein each ear cup comprises:
a housing having a mounting structure for mounting the ear cup on a wearable support;
a speaker;
an external power and signal connector;
a speaker drive circuit for operating the speaker; and
a power and signal cable that extends between the ear cups and is connected at each end to a respective external power and signal connector;
wherein the first ear cup further comprises:
a first profiled opening defining a mounting structure for mounting a removable control module having a shape corresponding to first profile and a corresponding power and signal connector onto the first ear cup, wherein the external power and signal connector of the first ear cup is configured to engage the corresponding power and signal connector of the removable control module so that the removable control module can provide operating signals to the speaker drive circuits of the first and second ear cups via the external power and signal connectors and the power and signal cable; and
wherein the second ear cup comprises:
a second profiled opening defining a mounting structure for mounting a removable battery pack having a shape corresponding to the second profiled opening and a corresponding power connector onto the second ear cup, wherein the external power and signal connector of the second ear cup is configured to engage the corresponding power connector on the removable battery pack so that the removable battery pack can provide power to the removeable control module and to the speaker drive circuits of the first and second ear cups via the external power and signal connectors and the power and signal cable; and wherein the first and second profile of the mounting structures on the first and second ear cups are substantially the same, and each external power and signal connector is located at substantially the same position within a respective profile This structure allows the functional characteristics of the head set to be changed by changing the control module without the need to change or duplicate common parts of the system.

The external power and signal connectors can comprise an array of electrical connectors for connection to corresponding electrical connectors on a corresponding external power connector of the removeable control module or removable battery pack. The array of electrical connectors can face upward so as to be engageable from above by the corresponding electrical connectors.

The external power and signal connectors can further comprise power and signal contacts that engage with corresponding power and signal contacts located in the profiled opening of the respective ear cup.

The external power and signal connectors can be releasably secured to a respective ear cup.

The external power and signal connectors can be mounted in an upper region of the profiled opening.

The configuration can be reversible so that in cases where the wearable support has a front and back, such as a helmet or cap, a user can decide which side is to have the control module (the "first" ear cup), and which side is to have the battery (the "second" ear cup).

The headset can include the wearable support, such as a headband or a helmet. The first and second ear cups and the power and signal cable can be provided already connected to the support, or separate for connection by the user before use.

The battery pack can be rechargeable.

The control module can further comprise a microphone. The microphone can include a moveable boom to allow for adjustment of the position of the microphone in use. The control module can further comprise a transmitting and/or receiving antenna. The control module can also include external operating switches or buttons for controlling the function of the control module.

The control module can comprise one or more of: communication circuitry allowing a user to communicate with users of corresponding communication equipment; a playback module allowing a user to listen to audio file content or audio broadcasts; and adaptive circuitry for supressing or enhancing predetermined external sounds. These can be provided as interchangeable modules for use on the first ear cup.

The invention also provides a kit comprising a headset, a control module for mounting in the first ear cup, and a battery pack for mounting in the second ear cup.

The invention also provides a control module for use with the headset, comprising a removable control module having power and signal connectors, wherein the removable control module has a profile corresponding to that of the mounting structure on the first ear cup such that power and signal connectors on the removable control module can engage the corresponding external power and signal connector in the first ear cup so that the removable control module can provide operating signals to the speaker drive circuits of the headset.

The invention also provides a battery pack for use with a headset as, comprising a removable battery pack having a power connector, wherein the removable battery pack has a profile corresponding to that of the mounting structure on the second ear cup such that a power connector on the battery pack can engage the corresponding external power connector in the second ear cup so that the removable battery pack can provide power to the headset.

Further aspects of the invention are disclosed in the following description.

DETAILED DESCRIPTION

Figure 1:
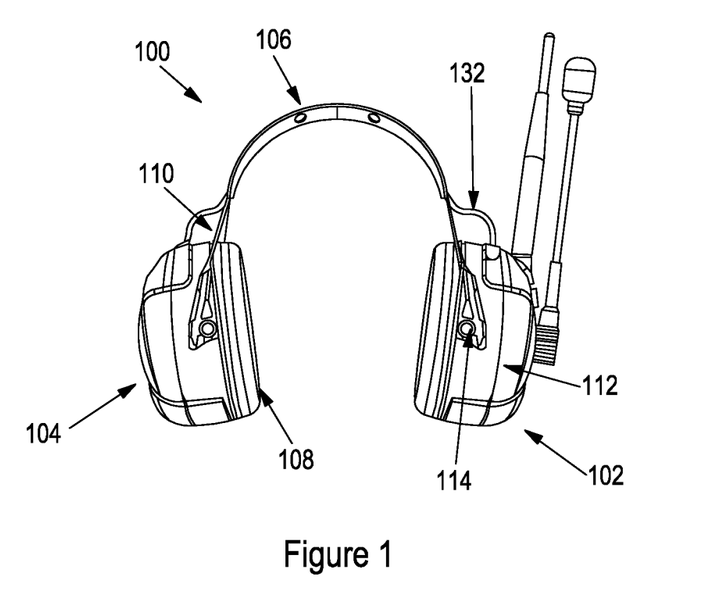
FIG. 1 is a front view of a headset.
Figure 2:
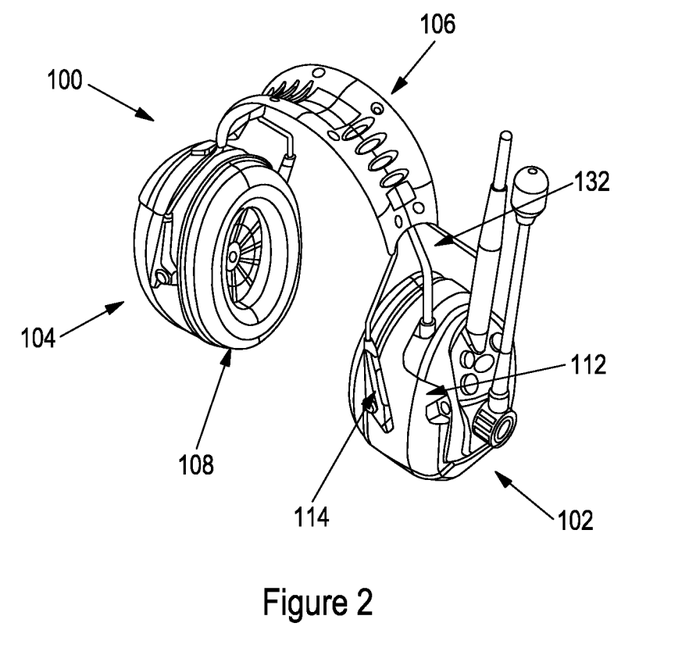
FIG. 2 is a perspective view of the headset of FIG. 1.

FIGS. 1 and 2 show a headset 100 comprising first and second ear cups 102, 104 connected to a headband 106. The ear cups 102, 104 are designed to fit over the ears of a user and are provided with foam cushion rings 108 to seat around the ear. The headband 106 includes a padded band mounted on a wire armature which forms Y-shaped arms 110 at each end for connection to the ear cups 106.

Each ear cup 102, 104 includes a shell 112 defining a housing. Mounting structures 114 are located on the outside of the shell 112 for connection to the Y-shaped arms of the headband 106. The connection allows the ear cups 102, 104 to pivot relative to the headband so that the ear cups 102, 104 can be positioned comfortably over the ears of a user.

Figure 3:
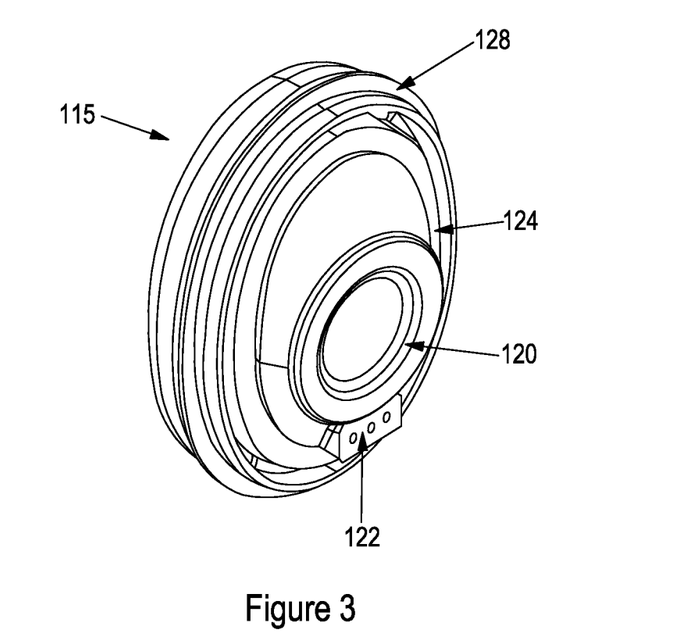
FIG. 3 shows a speaker plate for use in the headset of FIG. 1.

A speaker plate 115 is mounted in each ear cup 102, 104. The speaker plate includes a mounting ring 118 for connection to the shell 112 and a speaker drive 120 with connections 122 for receiving speaker drive signals for driving a speaker 124. FIG. 3 shows a rear view of the speaker plate 115.

Figure 4:
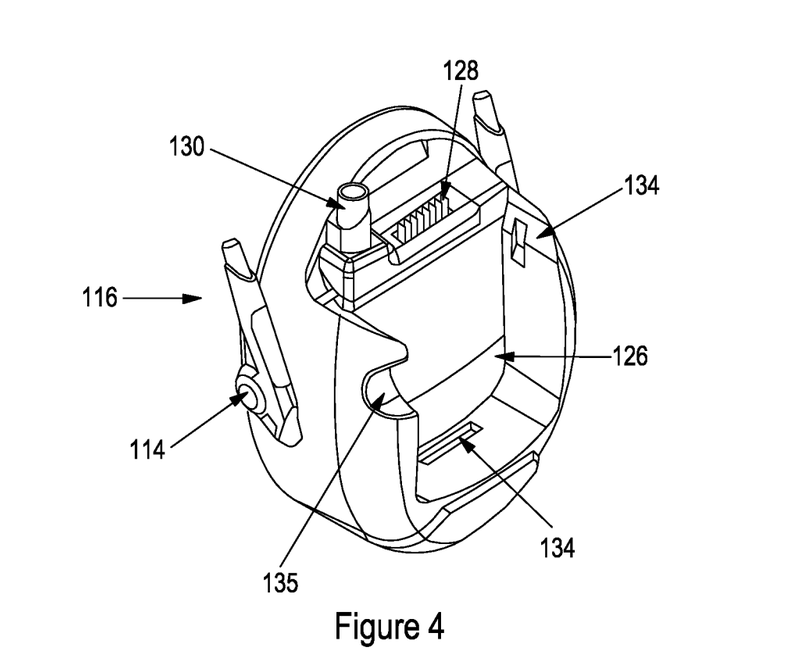
FIG. 4 shows a rear perspective view of an ear cup shell for use in the headset of FIG. 1.

FIG. 4 shows a rear view of a shell 116. In the headset of FIG. 1 the shell is the same for both ear cups 102, 104. The shell 116 houses electric circuitry that provides the speaker drive signals to the speaker 124. The back of the speaker defines a mounting structure in the form of a profiled opening 126. A set of external electrical power and signal connectors 128, and a power and signal cable connector 130 are located at the top of the profiled opening 126. The connectors 128 are in the form of an array of spring-loaded pin connectors (sometimes called "Pogo Pin" connectors). Each individual connector can be configured for a power and/or signal connection, as required. A power and signal cable 132 is connected to the cable connectors 130 on each ear cup 102, 104, and is secured to the headband 106, such that a speaker drive signal can be generated at one ear cup and communicated to the connections 122 in the other ear cup. By locating the power and signal connectors near the top of the profiled opening 126, complex routing of wiring through the shell 116 or profiled opening 126 can be avoided, further simplifying removal and replacement.

Figure 5:
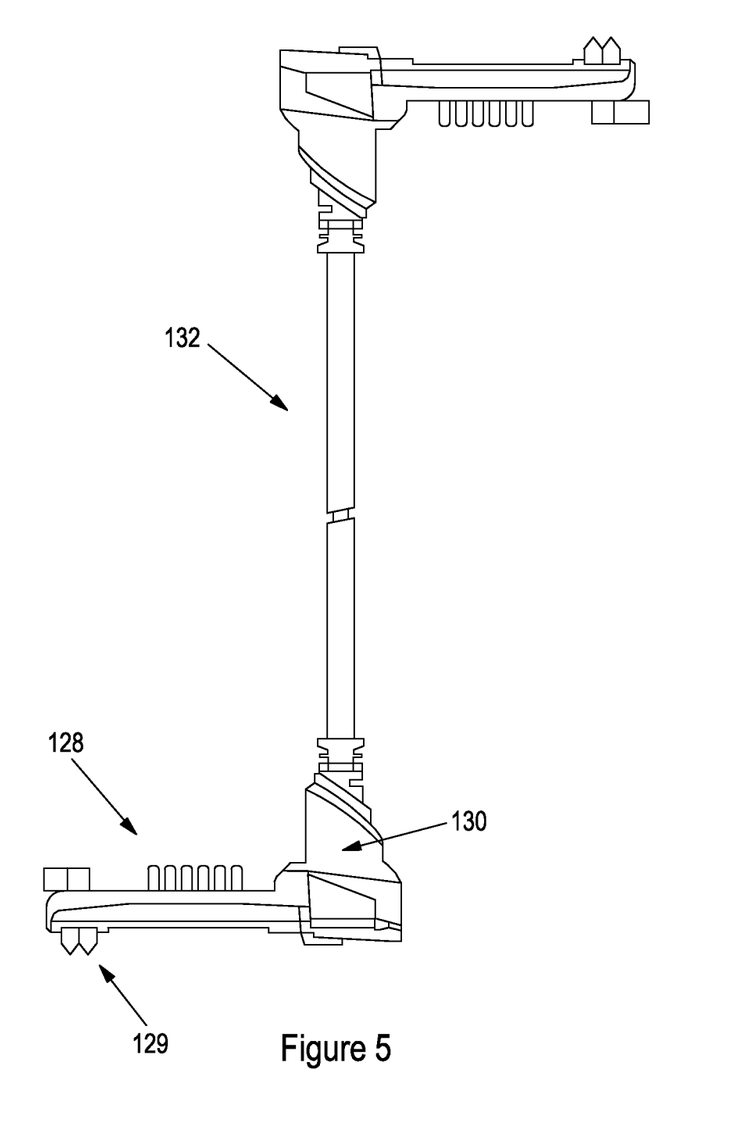
FIG. 5 shows a cable loom for mounting on the headset of FIG. 1.

FIG. 5 shows a loom comprising the cable 132 having a power and signal connector 128 connected at each end by means of a cable connector 130. Each connector also includes an electronic circuit (not shown) for handling the signals passing through the connector. A pair of power and signal contacts 129 is provided on the lower side of the connector 128.

Figure 6:
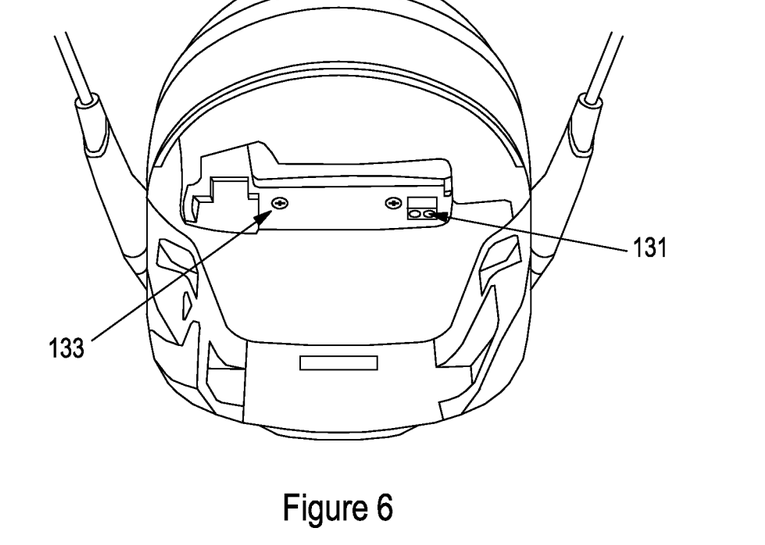
FIG. 6 shows a shell without the power and signal connector.

FIG. 6 shows a shell 116 without the power and signal connector 128. The power and signal connector 128 can secured to the shell by screws which engage in screw holes 133 so that the power and signal contacts 129 on the power and signal connector 128 engage corresponding contacts 131 in the shell 116 for providing signals to the speaker drive 120. This allows the power and signal connector 128 to be removed from the shell without the need to open the shell and disconnect the speaker drive. This can be useful if it becomes necessary to replace the loom due to damage or wear arising from use.

Figure 9:
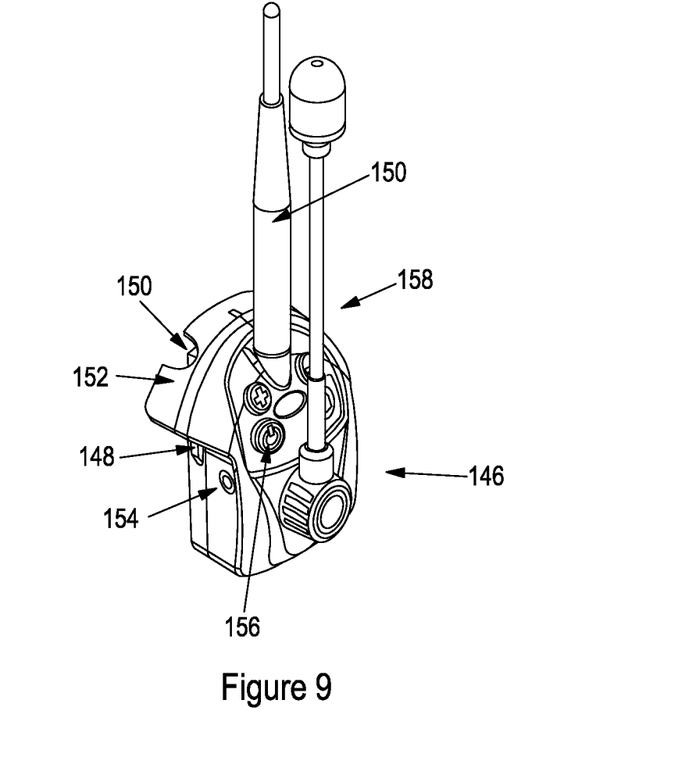
FIG. 9 shows a rear perspective view of a removable control module for use in the headset of FIG. 1.

The profiled opening 126 defines a space for receiving a removable module such as a rechargeable battery module (FIG. 7) or a control module (FIG. 9). Slots 134 are defined in the walls of the profiled opening 126 for receiving locating tabs on the module to hold it in place. A cut-out 135 is provided in the side wall of the shell 116 to allow access to the side of a removable module when located in the profiled opening 126.

Figure 7:
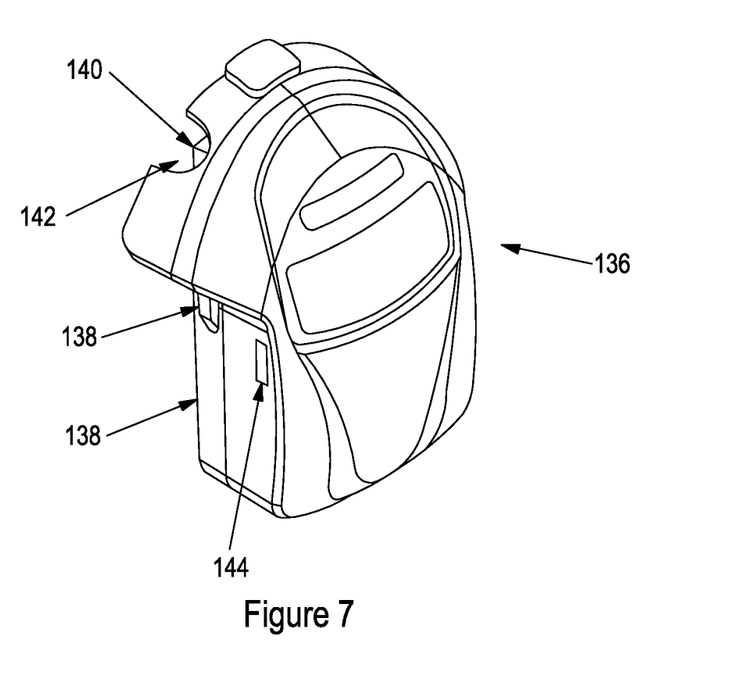
FIG. 7 shows a rear perspective view of a removable battery pack for use in the headset of FIG. 1.
Figure 8:
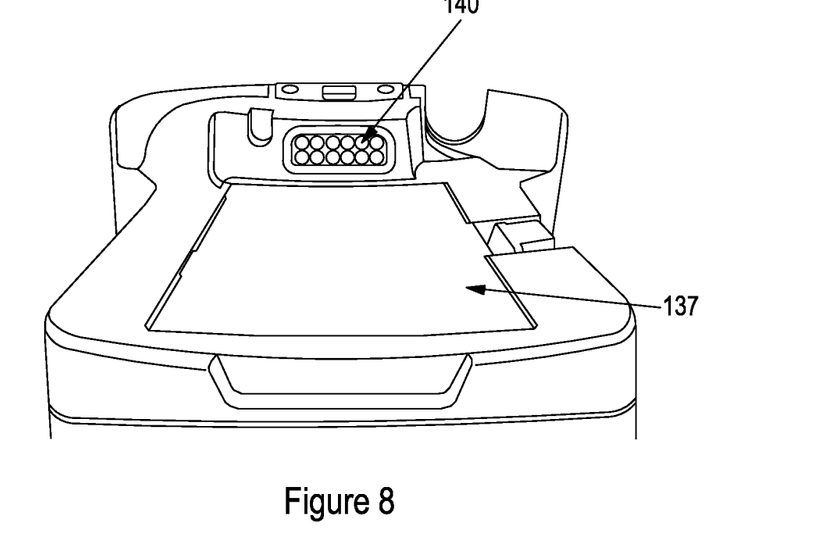
FIG. 8 shows the front view of the battery pack of FIG. 7.

FIG. 7 shows a rechargeable battery pack 136 as one of the removable modules. In the headset of FIG. 1, the battery pack 136 is shown in the second ear cup 104. The front face 137 of the battery pack 136 is shaped to correspond to the opening 126 in the shell 116 and has locating tabs 138 to engage in the slots 134. As is shown in FIG. 8, front face 137 of the battery pack 136 also includes power and signal connectors 140 in an upper region. The arrangement of the power and signal connectors 140 corresponds to the array on the power and signal connector 128 in the shell 116. The power and signal connectors 140 are positioned so that when the battery pack 136 is located in the profiled opening 126, the connectors 140 engages the power and signal connections 128 is the shell 116. The upper edge of the battery pack has a cut-out 142 to accommodate the cable connector 130. A charging connector 144, in this case a micro-USB connector, is located in the side of the battery pack 136 at a position that will align with the cut-out 135 in the shell 116 when the battery pack 136 is installed in the opening 126. This allows the battery to be connected to a power source for recharge without being removed from the shell 116. The battery pack 136 can be a Li-ion battery. Alternatively, a replaceable battery stack can be used, such as a number of AAA batteries in the pack that can be replaced via a removable hatch in the rear surface of the battery pack 136. The AAA batteries can be single use or rechargeable (either in situ, or externally). The user can not only replace one battery pack with another example of the same type (e.g. replace a discharged rechargeable battery pack with a fully charged battery pack allowing the original to be recharged separately), they can also replace, for example, a rechargeable battery pack with a pack comprising a stack of non-rechargeable batteries, or vice versa.

FIG. 9 shows a control module 146 forming the other removable module. In the headset of FIG. 1, the control module 146 is shown in the first ear cup 102. The front face of the control module 146 is shaped to correspond to the profiled opening 126 in the shell 116 and has locating tabs 148 to engage in the slots 134. The front face of the control module 146 also includes a power and signal connector 150 in an upper region. The power connector is positioned so that when the battery pack is located in the opening 126, the connector 150 engages the electrical connections 128 is the shell 116 in the same manner as described above in relation to the battery pack 136. The upper edge of the control module 146 has a cut-out 152 to accommodate the cable connector 130. An external signal input 154, in this case a miniature phone jack/socket connector (e.g. a 3.5 mm stereo audio socket), is located in the side of the control module 146 at a position that will align with the cut-out 135 in the shell 116 when the control module 146 is installed in the opening 126. This allows an external signal source to be connected to the control module 146 while it is located in the shell 116. The control module 146 contains control circuitry for providing speaker control signals for driving the speakers 124 in the ear cups 102, 104 via the corresponding power and signal connectors 150 and power and signal connectors 128 and cable 132. Power is provided from the battery pack 136 via the cable 132 and connectors 150 and power and signal connectors 128.

The rear surface of the control module 146 has control buttons 156 to control aspects of operation such as power on/off, volume, channel selection, etc., depending on the function of the control module.

The control module of FIG. 9 also includes an optional boom microphone 158 pivotally mounted on the rear surface of the control module 146, and an optional rf antenna 160 mounted at an upper edge of the control module 146 for receiving signals from, or transmitting signals to, users of corresponding communications equipment.

The functional characteristics of the control module 146 can be selected according to requirements. For example, the control module 146 can contain circuitry for communication to other headset users (or equivalent communications equipment) utilising the microphone 158 and antenna 160. A number of communication systems are available, such as the CARDO® Dynamic Mesh Communication (DMC), using Bluetooth® or other communication protocols. Such systems may be useful where users are in high noise environments and separated from other users (e.g. construction sites).

In another option, the control module 146 can simply allow playback of music or audio files, or connection to radio broadcasts, allowing the user to listen to audio content while working in a noisy environment.

A further option involves active management of two-way communication to apply frequency or signal level thresholds where the noise environment is highly variable (explosions, gunshots, periodic impact noise, etc.). In this case, input from the microphone can be used to adapt the speaker output or the application of noise cancelling processes.

Figure 10:
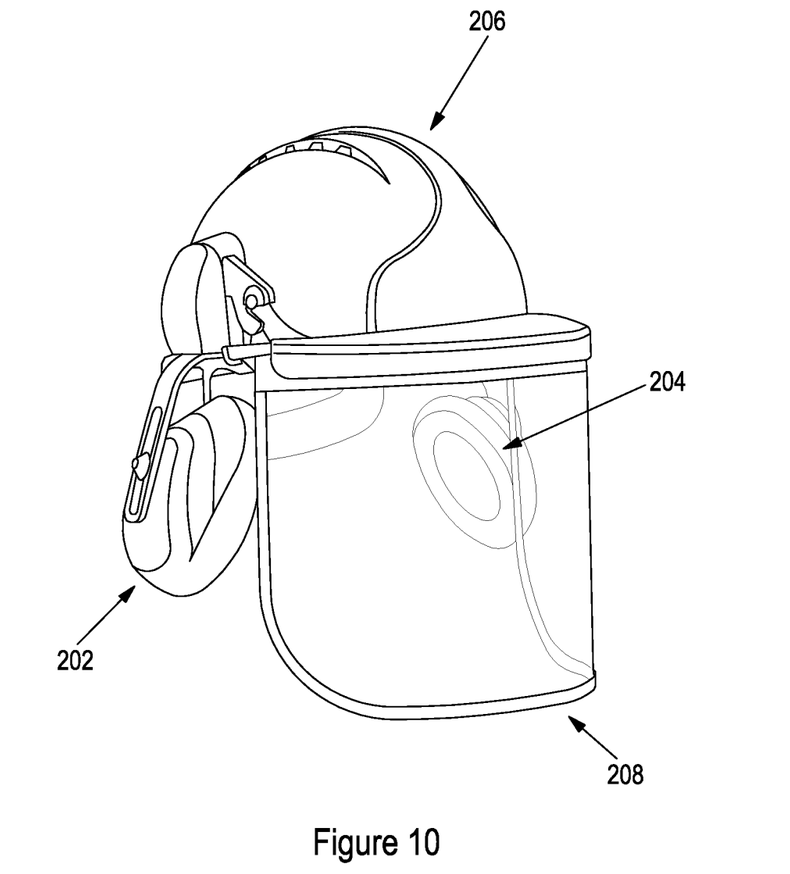
FIG. 10 shows a headset installed on a safety helmet.

The headset of FIG. 1 is easily reversible so that a user can choose to have the microphone on either the right or left. The pivotal mount of the microphone 158 (FIG. 9) allows the user to adjust the position of the microphone according to the side selected. A different headset is shown in FIG. 10. In this case, the ear cups 202, 204 are mounted directly onto a safety helmet 206 having a pivoting visor 208, instead of the headband of FIG. 1. The structure and function of the ear cups 202, 204 is the same as that of the ear cups 102, 104 of the headset of FIG. 1 but the particular manner of mounting the ear cups is different. Because the helmet of FIG. 10 has a distinct front and back direction, positioning of the microphone on one side or other is determined by which shell the control module is installed in. This is possible if the shells have the same shaped openings and positioning of contacts and connections, allowing both sides to be used as either battery or control module supports. In such a case, the ear cups could be provided for retrofitting an existing helmet, or integral with the helmet.

Whether or not the headband mounting or helmet (or other headwear) mounting is used, a user can initially specify one control module and then subsequently obtain other control modules that can be installed in place of the original one. Alternatively, a set of different modules can be supplied. Similarly, a single battery pack can be supplied, or multiple packs provided so that one can be recharging while the other is in use.

The invention claimed is:

1. A headset, comprising:
first and second ear cups, wherein each ear cup comprises:
a housing having a mounting structure for mounting the ear cup on a wearable support;
a speaker;
an external power and signal connector;
a speaker drive circuit for operating the speaker; and
a power and signal cable that extends between the ear cups and is connected at each end to a respective external power and signal connector;
wherein the first ear cup further comprises:
a first profiled opening defining a mounting structure for mounting a removable control module having a shape corresponding to first profile and a corresponding power and signal connector onto the first ear cup, wherein the external power and signal connector of the first ear cup is configured to engage the corresponding power and signal connector of the removable control module so that the removable control module can provide operating signals to the speaker drive circuits of the first and second ear cups via the external power and signal connectors and the power and signal cable; and
wherein the second ear cup comprises:
a second profiled opening defining a mounting structure for mounting a removable battery pack having a shape corresponding to the second profiled opening and a corresponding power connector onto the second ear cup, wherein the external power and signal connector of the second ear cup is configured to engage the corresponding power connector on the removable battery pack so that the removable battery pack can provide power to the removeable control module and to the speaker drive circuits of the first and second ear cups via the external power and signal connectors and the power and signal cable; and wherein the first and second profile of the mounting structures on the first and second ear cups are the same, and each external power and signal connector is located at the same position within a respective profile;

wherein the external power and signal connectors are mounted in an upper region of the respective profiled opening.

2. A headset as claimed in claim 1, further comprising a wearable support to which the first and second ear cups and the power and signal cable are connected.

3. A headset as claimed in claim 1, wherein each external power and signal connector comprises an array of electrical connectors for connection to corresponding electrical connectors on a corresponding external power connector of the removeable control module or removable battery pack.

4. A headset as claimed in claim 3, wherein the array of electrical connectors faces upward so as to be engageable from above by the corresponding electrical connectors.

5. A headset as claimed in claim 3, wherein each external power and signal connector further comprises power and signal contacts that engage with corresponding power and signal contacts located in the profiled opening of the respective ear cup.

6. A headset as claimed in claim 5, wherein the external power and signal connectors are releasably secured to a respective ear cup.

7. A headset as claimed in claim 1, further comprising a removeable control module mounted in the profiled opening of the first ear cup, and a removable battery pack mounted in the profiled opening of the second ear cup.

8. A headset as claimed in claim 7, wherein the control module comprises one or more of:
communication circuitry allowing a user to communicate with users of corresponding communication equipment;
a playback module allowing a user to listen to audio file content or audio broadcasts; and
adaptive circuitry for supressing or enhancing predetermined external sounds.

9. A headset as claimed in claim 8, comprising two or more of:
a first control module comprising communication circuitry allowing a user to communicate with users of corresponding communication equipment;
a second control module comprising a playback module allowing a user to listen to audio file content or audio broadcasts; and
a third control module comprising adaptive circuitry for supressing or enhancing predetermined external sounds;
wherein the first, second, and third modules are interchangeable on the first ear cup.

10. A kit comprising a headset as claimed in claim 1, a removeable control module for mounting in the first ear cup, and a removeable battery pack for mounting in the second ear cup.

11. A removeable control module for use with a headset as claimed in claim 1, comprising a removable control module body having corresponding power and signal connectors, wherein the removable control module body has a profile corresponding to that of the first profiled opening of the first ear cup such that the corresponding power and signal connectors on the removable control module are engageable with the external power and signal connector in the first ear cup so that the removable control module can provide operating signals to the speaker drive circuits of the headset.

12. A removeable control module as claimed in claim 11, wherein the control module comprises one or more of:
communication circuitry allowing a user to communicate with users of corresponding communication equipment;
a playback module allowing a user to listen to audio file content or audio broadcasts; and
adaptive circuitry for supressing or enhancing predetermined external sounds.

13. A removeable battery pack for use with a headset as claimed in claim 1, comprising a removable battery pack body having corresponding power connector, wherein the removeable battery pack body has a profile corresponding to that of the second profiled opening on the second ear cup such that the corresponding power connector on the removeable battery pack is engageable with the external power and signal connector in the second ear cup so that the removable battery pack can provide power to the headset.

\* \* \* \* \*